United States Patent
Monneret et al.

(10) Patent No.: US 6,878,746 B2
(45) Date of Patent: Apr. 12, 2005

(54) CARBAMATE AND THIOCARBAMATE PODOPHYLLOTOXIN DERIVATIVES, PREPARATION METHOD AND PHARMACEUTICAL COMPOSITIONS CONTAINING THEM

(75) Inventors: Claude Monneret, Paris (FR); Emmanuel Bertounesque, Paris (FR); Philippe Meresse, Salesches (FR); Ghanem Atassi, Cabrials (FR); Alain Pierre, Les Alluets le Roi (FR); John Hickman, Paris (FR); Bruno Pfeiffer, Saint Leu la Foret (FR); Pierre Renard, Le Chesnay (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 0 days.

(21) Appl. No.: 10/312,175

(22) PCT Filed: Jun. 19, 2001

(86) PCT No.: PCT/FR01/01908

§ 371 (c)(1),
(2), (4) Date: Dec. 20, 2002

(87) PCT Pub. No.: WO01/98307

PCT Pub. Date: Dec. 21, 2001

(65) Prior Publication Data

US 2004/0101574 A1 May 27, 2004

(30) Foreign Application Priority Data

Jun. 20, 2000 (FR) .............................. 00 07823

(51) Int. Cl.$^7$ .................. A61K 31/365; C07D 493/04
(52) U.S. Cl. ....................................... 514/468; 549/298
(58) Field of Search ........................ 549/298; 514/468

(56) References Cited

U.S. PATENT DOCUMENTS 6,566,393 B1 * 5/2003 Lee et al. ................... 514/463

FOREIGN PATENT DOCUMENTS

FR 1455540 12/1996
JP 1-117885 5/1989

OTHER PUBLICATIONS

Greenwald, R.B., et al. Chemical Abstracts Service, Database accession No. 132:15517.

* cited by examiner

Primary Examiner—Bernard Dentz
(74) Attorney, Agent, or Firm—The Firm of Hueschen and Sage

(57) ABSTRACT

A compound selected from these of formula (I):

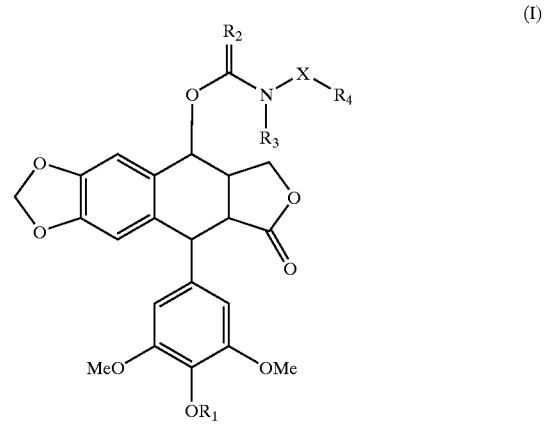

wherein:

$R_1$ represents hydrogen, alkyl, aryl, arylalkyl, heteroaryl, heteroarylalkyl, alkoxycarbonyl, aryloxycarbonyl, arylalkoxycarbonyl, heterocycloalkoxycarbonyl, alkylsulfonyl, arylsulfonyl, arylalkylsulfonyl or phosphono, $R_2$ represents oxygen or sulphur, $R_3$ represents hydrogen or alkyl, cycloalkyl or arylalkyl, X represents linear or branched ($C_1$–$C_6$)alkylene, $R_4$ represents a group selected from amino optionally substituted by one or two groups, —N($R_3$)—$X_1$—$OR_5$ wherein $R_3$, $X_1$ and $R_5$ are as defined in the description, —N($R_3$)—$X_1$—$NR_6R_7$ wherein $R_3$, $X_1$, $R_6$ and $R_7$ are as defined in the description, hydroxy, alkoxy, aryloxy, —O—$X_1$—$OR_5$ wherein $R_5$ and $X_1$ are as defined in the description, and —O—$X_1$—$NR_6R_7$ wherein $R_6$, $R_7$ and $X_1$ are as defined in the description, its isomers, and also addition salts thereof with a pharmaceutically acceptable acid or base, and medical products containing the same which are useful in the treatment of cancer.

10 Claims, No Drawings

CARBAMATE AND THIOCARBAMATE PODOPHYLLOTOXIN DERIVATIVES, PREPARATION METHOD AND PHARMACEUTICAL COMPOSITIONS CONTAINING THEM

This application is a 371 of PCT/FR01/01908 filed Jun. 19, 2001.

The present invention relates to new carbamate and thiocarbamate podophyllotoxin compounds, to a process for their preparation and to pharmaceutical compositions containing them.

The compounds of the invention are derivatives of podophyllotoxin, a natural lignan known for its use in the treatment of cancer. Other synthetic derivatives, such as etoposide and teniposide, are currently used as chemotherapeutic agents in the treatment especially of small-cell lung cancer. Those various compounds act by inhibiting the catalytic activity of topoisomerase II.

Various modifications have been made to those compounds, such as the modifications described in the Patent Applications JP 948 782, WO 97/13776 and U.S. Pat. No. 3,634,459. Nevertheless, anti-cancer therapeutic requirements call for the constant development of new anti-tumour and cytotoxic agents with the aim of obtaining medicaments that are simultaneously more active, more soluble and better tolerated.

In addition to the fact that the compounds of the present invention are new, they have a surprising in vitro and in vivo activity that is superior to that observed hitherto. The compounds discovered by the Applicant accordingly have properties that render them particularly useful in the treatment of cancers.

More especially, the present invention relates to the compounds of formula (I):

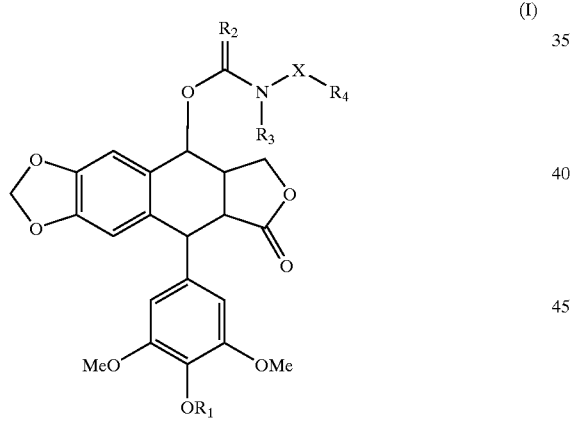

wherein:
$R_1$ represents a group selected from hydrogen, linear or branched $(C_1-C_6)$alkyl, aryl, aryl-$(C_1-C_6)$alkyl in which the alkyl moiety may be linear or branched, heteroaryl, heteroaryl-$(C_1-C_6)$alkyl in which the alkyl moiety may be linear or branched, linear or branched $(C_1-C_6)$alkoxycarbonyl, aryloxycarbonyl, aryl-$(C_1-C_6)$alkoxycarbonyl in which the alkoxy moiety may be linear or branched, heterocycloalkoxycarbonyl, linear or branched $(C_1-C_6)$alkylsulfonyl, arylsulfonyl, aryl-$(C_1-C_6)$alkylsulfonyl in which the alkyl moiety may be linear or branched, and phosphonic,
$R_2$ represents an oxygen atom or a sulphur atom,
$R_3$ represents a hydrogen atom, a linear or branched $(C_1-C_6)$ alkyl group, a cycloalkyl group or an aryl-$(C_1-C_6)$alkyl group in which the alkyl moiety may be linear or branched,
X represents a linear or branched $(C_1-C_6)$alkylene group,
$R_4$ represents a group selected from:
amino optionally substituted by one or two identical or different groups selected from linear or branched $(C_1-C_6)$alkyl, aryl and aryl-$(C_1-C_6)$alkyl in which the alkyl moiety may be linear or branched,
a group of formula —$N(R_3)$—$X_1$—$OR_5$ wherein $R_3$ is as defined hereinbefore, $X_1$ represents a linear or branched $(C_1-C_6)$alkylene group and $R_5$ represents a group selected from hydrogen, linear or branched $(C_1-C_6)$alkyl, aryl and aryl-$(C_1-C_6)$alkyl in which the alkyl moiety may be linear or branched,
a group of formula —$N(R_3)$—$X_1$—$NR_6R_7$ wherein $R_3$ and $X_1$ are as defined hereinbefore and $R_6$ and $R_7$, which may be identical or different, each represents a group selected from hydrogen, linear or branched $(C_1-C_6)$alkyl, aryl and aryl-$(C_1-C_6)$alkyl in which the alkyl moiety may be linear or branched,
hydroxy,
linear or branched $(C_1-C_6)$alkoxy,
aryloxy,
a group of formula —O—$X_1$—$OR_5$ wherein $R_5$ and $X_1$ are as defined herein-before,
and a group of formula —O—$X_1$—$NR_6R_7$ wherein $R_6$, $R_7$ and $X_1$ are as defined hereinbefore,
to their isomers, and to addition salts thereof with a pharmaceutically acceptable acid or base,
wherein:
aryl denotes a group selected from phenyl, biphenyl, naphthyl, dihydronaphthyl, tetrahydronaphthyl, indenyl, indanyl and benzocyclobutyl, each of those groups optionally having one or more identical or different substituents selected from halogen, hydroxy, linear or branched $(C_1-C_6)$alkyl, linear or branched $(C_1-C_6)$alkoxy, cyano, nitro, amino, linear or branched $(C_1-C_6)$alkylamino, linear or branched di-$(C_1-C_6)$ alkylamino, carboxy, linear or branched $(C_1-C_6)$ alkoxycarbonyl, linear or branched $(C_1-C_6)$ trihaloalkyl, linear or branched $(C_1-C_6)$ alkylcarbonyloxy, linear or branched $(C_1-C_6)$ alkylcarbonyl, and aminocarbonyl in which the amino moiety is optionally substituted by one or two identical or different linear or branched $(C_1-C_6)$alkyl groups,
heteroaryl denotes an aromatic monocyclic group, an aromatic bicyclic group, or a bicyclic group in which one of the rings is aromatic and the other ring is partially hydrogenated, having from 5 to 12 ring members, containing in the ring system one, two or three hetero atoms selected from oxygen, nitrogen and sulphur, it being possible for the said heteroaryl optionally to be substituted by the same substituents as those decribed in the case of the aryl group,
cycloalkyl denotes a monocyclic or bicyclic group that is saturated or unsaturated, but not of aromatic character, that contains from 3 to 10 carbon atoms and is optionally substituted by one or more identical or different groups selected from halogen, linear or branched $(C_1-C_6)$alkyl, linear or branched $(C_1-C_6)$trihaloalkyl, hydroxy, amino, linear or branched $(C_1-C_6)$alkylamino and linear or branched di-$(C_1-C_6)$alkylamino,
heterocycloalkyl denotes a cycloalkyl group as defined above containing in the ring system one or two hetero atoms selected from oxygen, nitrogen and sulphur, the said heterocycloalkyl being optionally substituted by one or more substituents such as those described in the case of the cycloalkyl group.

Isomers are to be understood as meaning the enantiomers and the diastereoisomers.

Among the pharmaceutically acceptable acids there may be mentioned, without implying any limitation, hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid, etc.

Among the pharmaceutically acceptable bases there may be mentioned, without implying any limitation, sodium hydroxide, potassium hydroxide, triethylamine, tert-butylamine, etc.

The substituent $R_1$ preferred according to the invention is the hydrogen atom.

The substituent $R_2$ preferred according to the invention is the oxygen atom.

Very advantageously, preferred compounds of the invention are the compounds of formula (I) wherein X represents a linear ($C_2$–$C_4$)alkylene group.

Substituents $R_3$ preferred according to the invention are the hydrogen atom and the linear or branched ($C_1$–$C_6$)alkyl group.

According to an advantageous embodiment of the invention, preferred compounds of the invention are the compounds of formula (I) wherein $R_4$ represents a group selected from:
  amino substituted by one or two identical or different linear or branched ($C_1$–$C_6$)alkyl groups,
  a group of formula —N($R_3$)—$X_1$—$OR_5$ wherein $R_3$ represents a hydrogen atom or a linear or branched ($C_1$–$C_6$)alkyl group and $X_1$ and $R_5$ are as defined for formula (I),
  and a group of formula —O—$X_1$—$OR_5$ wherein $X_1$ and $R_5$ are as defined for formula (I).

Especially advantageously, preferred compounds of the invention are the compounds of formula (I) wherein $R_4$ represents a group —N($R_3$)—$X_1$—$OR_5$ or —O—$X_1$—$OR_5$ wherein $R_3$ represents a hydrogen atom, $X_1$ represents a linear ($C_2$–$C_4$)alkylene chain and $R_5$ represents a hydrogen atom.

Preferred compounds of the invention are:
  (5S,5aS,8aS,9R)-9-(4-hydroxy-3,5-dimethoxyphenyl)-8-oxo-5,5a,6,8,8a,9-hexahydro-furo [3',4':6,7]naphtho[2,3-d][1,3]dioxol-5-yl 2-(dimethylamino)ethyl(methyl)carbamate,
  (5S,5aS,8aR,9R)-9-(4-hydroxy-3,5-dimethoxyphenyl)-8-oxo-5,5a,6,8,8a,9-hexahydro-furo [3',4':6,7]naphtho[2,3-d][1,3]dioxol-5-yl 2-(dimethylamino)ethyl(methyl)carbamate,
  (5S,5aS,8aS,9R)-9-(4-hydroxy-3,5-dimethoxyphenyl)-8-oxo-5,5a,6,8,8a,9-hexahydro-furo [3',4':6,7]naphtho[2,3-d][1,3]dioxol-5-yl 3-(dimethylamino)propylcarbamate,
  (5S,5aS,8aS,9R)-9-(4-hydroxy-3,5-dimethoxyphenyl)-8-oxo-5,5a,6,8,8a,9-hexahydro-furo [3',4':6,7]naphtho[2,3-d][1,3]dioxol-5-yl 2-(2-hydroxyethoxy)ethylcarbamate,
  (5S,5aS,8aS,9R)-9-(4-hydroxy-3,5-dimethoxyphenyl)-8-oxo-5,5a,6,8,8a,9-hexahydro-furo[3',4':6,7]naphtho[2,3-d][1,3]dioxol-5-yl 2-[(2-hydroxyethyl)amino]ethylcarbamate,
  (5S,5aS,8aS,9R)-9-(4-hydroxy-3,5-dimethoxyphenyl)-8-oxo-5,5a,6,8,8a,9-hexahydro-furo [3',4':6,7]naphtho[2,3-d][1,3]dioxol-5-yl-2-(dimethylamino)ethylcarbamate.

The isomers and the addition salts with a pharmaceutically acceptable acid or base of the preferred compounds form an integral part of the invention.

The present invention extends also to a process for the preparation of the compounds of formula (1), which process is characterised in that there is used as starting material a compound of formula (II):

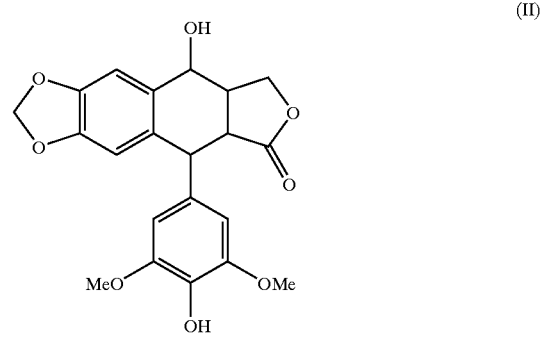

(II)

which is subjected under basic conditions:

either to the action of a compound of formula (III):

(III)

wherein $R'_1$ represents a group selected from linear or branched ($C_1$–$C_6$)alkyl, aryl, aryl-($C_1$–$C_6$)alkyl in which the alkyl moiety may be linear or branched, heteroaryl, heteroaryl-($C_1$–$C_6$)alkyl in which the alkyl moiety may be linear or branched, linear or branched ($C_1$–$C_6$) alkylcarbonyl, arylcarbonyl, aryl-($C_1$–$C_6$)alkylcarbonyl in which the alkyl moiety may be linear or branched, heterocycloalkylcarbonyl, linear or branched ($C_1$–$C_6$) alkylsulfonyl, arylsulfonyl, and aryl-($C_1$–$C_6$)alkylsulfonyl in which the alkyl moiety may be linear or branched, and X represents a hydrogen atom or a halogen atom, to yield the compounds of formula (IV/A):

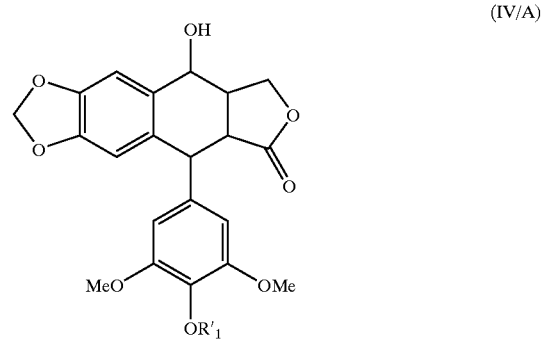

(IV/A)

wherein $R'_1$ is as defined hereinbefore, or to the action of a compound of formula (V):

(V)

wherein G represents a conventional protecting group for hydroxy functions and L represents a leaving group custom ary in organic chemistry,
to yield the compounds of formula (IV/B):

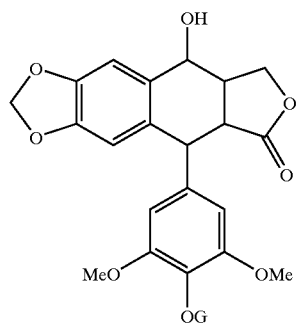

(IV/B)

wherein G is as defined hereinbefore,
the totality of the compounds of formulae (IV/A) and (IV/B) constituting the compounds of formula (IV):

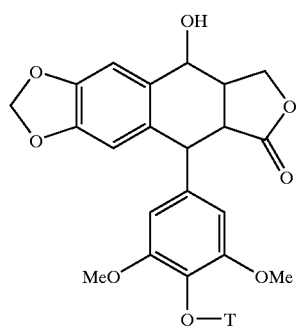

(IV)

wherein T represents a group $R'_1$ or G as defined hereinbefore, which compound of formula (IV) is treated in basic medium with a compound of formula (VI):

$$Ph—O—C(R_2)Cl \quad (VI)$$

wherein Ph represents an optionally substituted phenyl group and $R_2$ represents an oxygen atom or a sulphur atom, to yield the compounds of formula (VII):

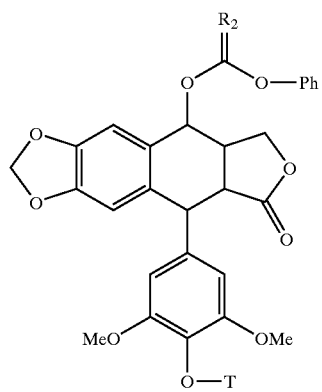

(VII)

wherein T, Ph and $R_2$ are as defined hereinbefore,
which compound of formula (VII) is reacted in basic medium with a compound of formula (VIII):

$$R_4—X—NH—R_3 \quad (VIII)$$

wherein $R_4$, $R_3$ and X are as defined for formula (I), to yield, respectively, the compounds of formula (1/a), a particular case of the compounds of formula (I), or the compounds of formula (IX), according to whether T represents a group $R'_1$ or a group G,

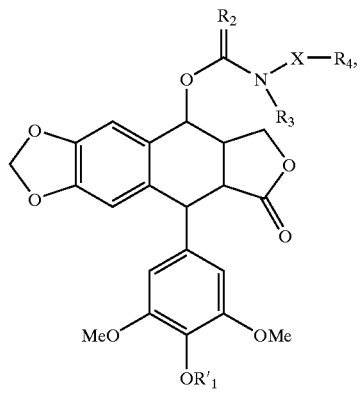

(I/a)

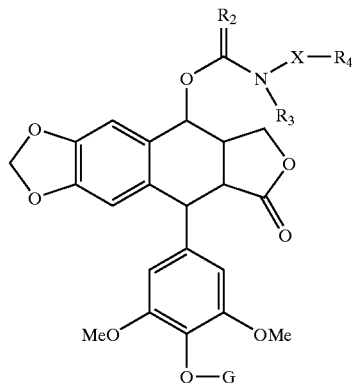

(IX)

wherein $R'_1$, G, $R_2$, $R_3$, $R_4$ and X are as defined hereinbefore,
the hydroxy function of which compounds of formula (IX) is deprotected according to conventional methods of organic chemistry to yield the compounds of formula (I/b), a particular case of the compounds of formula (I):

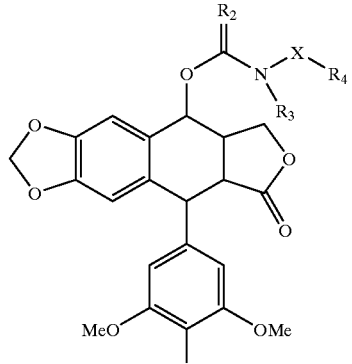

(I/b)

wherein $R_2$, $R_3$, $R_4$ and X are as defined for formula (I),
the compounds (I/a) and (I/b) constituting the totality of the compounds of the invention, which compounds are purified, if necessary, according to a conventional purification technique, may be separated, if desired, into their different isomers according to a conventional separation technique, and are converted, if desired, into their addition salts with a pharmaceutically acceptable acid or base.

The compounds of formulae (II), (V), (VI) and (VIII) are either commercially available compounds, or are obtained according to conventional methods of organic synthesis.

The compounds of formula (I) exhibit especially valuable anti-tumour properties. They have an excellent cytotoxicity in vitro on cell lines from murine and human tumours and are active in vivo. The characteristic properties of these compounds enables them to be used therapeutically as anti-tumour agents.

The present invention relates also to pharmaceutical compositions comprising as active ingredient at least one compound of formula (I), its optical isomers or one of its addition salt with a pharmaceutically acceptable acid or base, alone or in combination with one or more pharmaceutically acceptable, inert, non-toxic excipients or carriers.

Among the compositions according to the invention there may be mentioned more especially those which are suitable for oral, parenteral (intravenous, intramuscular or subcutaneous) per- or trans-cutaneous, nasal, rectal, perlingual, ocular or respiratory administration, and especially tablets or dragees, sublingual tablets, soft gelatin capsules, hard gelatin capsules, suppositories, creams, ointments, dermal gels, injectable or drinkable preparations, aerosols, eye or nose drops, etc.

The useful dosage varies in accordance with the the age and weight of the patient, the administration route, the nature and the severity of the disorder and the administration of possible associated treatments and ranges from 0.5 mg to 500 mg per day in one or more administrations.

The following Examples illustrate the invention but do not limit it in any way. The starting materials employed are either known products or are products prepared according to known procedures.

Preparation 1:(5S,5aS,8aS,9R)-9-(4-{[(Benzyloxy) carbonyl]oxy}-3,5-dimethoxyphenyl)-8-oxo5,5a,6,8,8a,9-hexahydro-furo[3',4':6,7]naphtho[2,3-d][1,3]dioxol-5-yl 4-nitrophenyl carbonate Step 1: 4-[(5R,5aS,8aS,9S)-9-Hydroxy-6-oxo-5,5a,6,8,8a,9-hexahydro-furo [3',4':6, 7]naphtho[2,3-d][1,3]dioxol-5-yl]-2,6-dimethoxyphenyl benzyl carbonate 0.55 mmol of triethylamine and 0.37 mmol of benzyl chloroformate are added in succession to a solution of 0.25 mmol of (5R,5aS,8aS,9S)-9-hydroxy-5-(4-hydroxy-3,5-dimethoxyphenyl)-5,8,8a,9-tetrahydrofuro[3',4':6,7]naphtho [2,3-d][1,3]dioxol-6(5aH)-one in 10 ml of anhydrous dichloromethane at 0° C. and under argon. After stirring for 1 hour, the reaction mixture is washed with water. The organic phase is then dried, filtered and subsequently concentrated under reduced pressure. Chromatography on silica gel (cyclohexane/ethyl acetate: 60/40) enables the expected product to be isolated.

Step 2: (5S, 5aS,8aS,9R)-9-(4-[[(Benzyloxy)carbonyl] oxy]-3,5-dimethoxyphenyl)-8-oxo-5,5a, 6,8,8a, 9-hexahydro-furo[3',4':6, 7]naphtho[2,3-d][1,3]dioxol-5-yl 4-nitrophenyl carbonate 0.155 ml of anhydrous pyridine is added to a solution of 1.71 mmol of p-nitrophenyl chloroformate in 5 ml of anhydrous dichloromethane. A white precipitate is formed in the reaction mixture. A solution of 0.502 mmol of the compound obtained in Step 1 in 5 ml of dichloromethane is then added dropwise under argon. Stirring is carried out for 45 minutes at ambient temperature, then 15 ml of water are poured into the reaction mixture. The organic phase is washed with water, dried over $MgSO_4$, filtered and concentrated under recued pressure. Chromatography on silica gel (cyclohexane/ethyl acetate: 4/1) enables the expected product to be isolated.

Melting point=125–130° C.

EXAMPLE 1

(5S,5aS,8aS,9R)-9-(4-Hydroxy-3,5-dimethoxyphenyl)-8-oxo-5,5a,6,8,8a,9-hexahydro-furo[3',4':6,7]naphtho[2,3-d][1,3] dioxol-5-yl 2-(dimethylamino)ethyl(methyl)carbamate Step 1: 4-[(5R,5aS, 8aS, 9S)-9-({[[2-(Dimethylamino) ethyl](methyl)amino]-carbonyl}oxy)-6-oxo-5,5a,6,8,8a,9-hexahydro-furo[3,4':6,7]-naphtho[2,3-d][1,3]dioxol-5-yl]-2, 6-dimethoxyphenyl benzyl carbonate 0.228 mmol of N,N,N'-trimethylethylenediamine and 0.228 mmol of triethylamine are added in succession to a solution of 0.171 mmol of the compound of Preparation 1 in 5 ml of anhydrous dichloromethane at ambient temperature and under argon. After stirring for one hour, the reaction mixture is hydrolysed. The organic phase is subsequently washed with water, then dried over $MgSO_4$, filtered and concentrated under reduced pressure. Chromatography on silica gel (dichloromethane/methanol: 97/3) enables the expected product to be isolated.

Melting point=102–103° C.

Step 2: (5S,5aS,8aS,9R)-9-(4-Hydroxy-3,5-dimethoxyphenyl)-8-oxo-5,5a, 6,8,8a,9-hexahydro-furo[3', 4':6, 7]naphtho [2,3-d][1,3]dioxol-5-yl 2-(dimethylamino) ethyl(methyl)carbamate 5% palladium-on-carbon (90.8 mg) is added to a solution of 0.138 mmol of the compound obtained in Step 1 in 8 ml of ethyl acetate. The reaction mixture is stirred under a hydrogen atmosphere (atmospheric pressure) for 1 hour 45 minutes, then filtered over Celite to remove the catalyst. The filtrate is then concentrated under reduced pressure. The crude residue is chromatographed on silica gel (dichloromethane/methanol: 96/4), enabling isolation of the expected product.

Melting point=184–186° C.

Mass spectrum (ES/MS): m/z=529 [M+H]$^+$, 551 [M+Na]$^+$

EXAMPLE 2

(5S,5aS,8aR,9R)-9-(4-Hydroxy-3,5-dimethoxyphenyl)-8-oxo-5,5a,6,8,8a,9-hexahydro-furo[3',4':6,7]naphtho[2,3-d][1,3]dioxol-5-yl 2-(dimethylamino)ethyl(methyl)carbamate Step 1: 4-[(5R,5aR,8aS,9S)-9-({[[2-(Dimethylamino) ethyl](methyl)-amino]carbonyl}oxy)-6-oxo-5,5a,6,8S8a,9-hexahydro-furo-[3',4':6, 7]naphtho[2,3-d][1,3]dioxol-5-yl]-2,6-dimethoxyphenyl benzyl carbonate 0.184 mmol of N,N,N'-trimethylethylenediamine and 0.184 mmol of triethylamine are added in succession to a solution of 0.141 mmol of the compound of Preparation 1 in 4 ml of anhydrous dichloromethane. After stirring for 2 hours 30 minutes at ambient temperature under argon there are added to the reaction mixture 3 ml of tetrahydrofuran and a 1M solution of tetrabutylammonium fluoride (0.285 mmol) in tetrahydrofuran. After reaction for 2 hours, 0.3 mmol of tetrabutylammonium fluoride is added. Stirring is carried out for 3 hours 30 minutes and the reaction mixture is poured into water (15 ml) and diluted with dichloromethane (10 ml). The aqueous phase is extracted with dichloromethane and the combined organic phases are washed with water and a saturated aqueous solution of NaCl, and then dried over $MgSO_4$, filtered and concentrated under reduced pressure. Chromatography on silica gel (dichloromethane/methanol: 97/3) enables the expected product to be isolated.

Mass spectrum (DCI/NH$_3$): m/z=663 [M+H]$^{30}$

Step 2: (5S,5aS,8aR,9R)-9-(4-Hydroxy-3,5-dimethoxyphenyl)-8-oxo-5,5a,6,8,8a,9-hexahydro-furo[3', 4':6, 7]naphtho[2,3-d][1,3]dioxol-5-yl 2-(dimethylamino) ethyl(methyl)carbamate The product is obtained in accordance with the procedure in Step 2 of Example 1, using as substrate the compound obtained in the above Step 1.

Mass spectrum (DCI/NH$_3$): m/z=529 [M+H]$^+$

EXAMPLE 3

(5S,5aS,8aS,9R)-9-(4-Hydroxy-3,5-dimethoxyphenyl)-8-oxo-5,5a,6,8,8a,9-hexahydro-furo[3',4':6,7]naphtho[2,3-d][1,3]dioxol-5-yl 3-(dimethylamino)propylcarbamate The product is obtained in accordance with the procedure in Example 1, Steps 1 and 2, using dimethylaminopropylamine instead of N,N,N'-trimethylethylenediamine as the reagent in Step 1.

$[\alpha]_D$ (CHCl$_3$)=−23° Mass spectrum (DCI/NH$_3$): m/z=529 [M+H]$^+$

EXAMPLE 4

(5S,5aS,8aS,9R)-9-(4-Hydroxy-3,5-dimethoxyphenyl)-8-oxo-5,5a,6,8,8a,9-hexahydro-furo[3',4':6,7]naphtho[2,3-d][1,3]dioxol-5-yl 2-(2-hydroxyethoxy)ethylcarbamate The product is obtained in accordance with the procedure in Example 1, Steps 1 and 2, using 2-aminoethoxyethanol instead of N,N,N'-trimethylethylenediamine as the reagent in Step 1.

Mass spectrum (DCI/NH$_3$): m/z=683 [M+NH$_4$]$^+$

EXAMPLE 5

(5S,5aS,8aS,9R)-9-(4-Hydroxy-3,5-dimethoxyphenyl)-8-oxo-5,5a,6,8,8a,9-hexahydro-furo[3',4':6,7]naphtho[2,3-d][1,3]dioxol-5-yl 2-[(2-hydroxyethyl)amino]ethylcarbamate The product is obtained in accordance with the procedure in Example 1, Steps 1 and 2, using 2-aminoethylaminoethanol instead of N,N,N'-trimethylethylenediamine as the reagent in Step 1.

EXAMPLE 6

(5S,5aS,8aS,9R)-9-(4-Hydroxy-3,5-dimethoxyphenyl)-8-oxo-5,5a,6,8,8a,9-hexahydro-furo[3',4':6,7]naphtho[2,3-d][1,3]dioxol-5-yl-2-(dimethylamino)ethylcarbamate The product is obtained in accordance with the procedure in Example 1, Steps 1 and 2, using dimethylaminoethylamine instead of N,N,N'-trimethylethylenediamine as the reagent in Step 1.

Pharmacological Study of the Compounds of the Invention

EXAMPLE 7

In Vitro Activity

The compounds of the invention were tested on various human and murine cell lines:

murine leukaemia L1210, epidermoid carcinoma A-431, non-small-cell lung carcinoma A549, small-cell lung carcinoma H69, colon carcinoma HT29, buccal epidermoid carcinoma KB-3-1.

The cells are cultured in RPMI 1640 complete culture medium comprising 10% foetal calf serum, 2 mM glutamine, 50 units/ml of penicillin, 50 µg/ml of streptomycin and 10 mM Hepes, pH 7.4. The cells are distributed on microplates and are exposed to the cytotoxic compounds for four doubling periods, that is to say 48 hours or 96 hours. The number of viable cells is then quantified by a colorimetric assay, the Microculture Tetrazolium Assay (J. Carmichael et al., Cancer Res.; 47, 936–942, (1987)). The results are expressed as IC$_{50}$, the cytotoxic concentration that inhibits the proliferation of the treated cells by 50%.

In these tests, the compound of Example 6 has the following IC$_{50}$ values:

| | IC$_{50}$ (µM) | | | | | |
|---|---|---|---|---|---|---|
| | L1210 | A-431 | A549 | H69 | HT29 | KB-3-1 |
| Example 6 | 0.038 | 0.071 | 0.046 | 0.096 | 0.121 | 0.085 |

EXAMPLE 8

Action on the Cell Cycle

L1210 cells are incubated for 21 hours at 37° C. in the presence of various concentrations of test compounds. The cells are then fixed using 70% ethanol (v/v), washed twice in PBS and incubated for 30 minutes at 20° C. in PBS that contains 100 µg/ml of RNAse and 50 µg/ml of propidium iodide. The results are expressed as a percentage of the cells that have accumulated in the G2+M phase after 21 hours compared with the control (control: 20%). At a concentration of 100 nM, the compound of Example 6 induces an 86% accumulation of the cells in the G2+M phase after 21 hours.

EXAMPLE 9

In Vivo Activity

*Anti-tumour Activity of the Compounds on P388 Leukaemia:

Line P388 (murine leukaemia) was supplied by the National Cancer Institute (Frederick, USA). The tumour cells (10$^6$ cells) were inoculated on day 0 into the peritoneal cavity of female BDF1 mice (Iffa–Credo, France) weighing from 18 to 20 g (groups of 6 animals).

The products were administered by the intravenous route on day 1.

The anti-tumour activity is expressed as % T/C:

$$\% \ T/C = \frac{\text{Median survival time of the treated animals}}{\text{Median survival time of the control animals}} \times 100$$

For information only, the compound of Example 6 is active against P388 leukaemia and induces a T/C of 203% at 6.25 mg/kg.

*Anti-tumour Activity of the Compounds on Lewis Lung Carcinoma:

Lewis lung carcinoma (LLC) is a solid tumour that appeared spontaneously in the lungs of a C57B1/6 mouse and is maintained by successive transplants of fragments by the s.c. route. The LLC was obtained from the Division of Cancer Treatment, Tumor Repository, National Cancer Institute, Frederick, Md., USA. The mice, which are 4 to 6 weeks old, were obtained from Iffa Credo (Lyon, France), and weighed from 20 to 22 g at the beginning of the experiment.

On the first day of the experiment (D0), the tumours are removed and cut into fragments of approximately 30 mg which are immediately grafted by the s.c. route into the B6D2F1 mice. The mice into which the fragments have been implanted are then randomly divided into the treated groups and the control group (7 animals per group).

The parameter used for evaluating the anti-tumour activity is the increase in survival time.

In addition, the number of surviving animals in each group is counted at the end of the experiment on day 90.

The products were administered in accordance with the scheme shown below. The results are expressed as % T/C, calculated in the same manner as in the preceding test:

| Product | Dose (mg/kg) | Route | Scheme | T/C % | Survivors D90 |
|---|---|---|---|---|---|
| Example 1 | 25 | i.v. | D 4, 8, 12 | 165 | 1/7 |
| Example 6 | 3.12 | i.v. | D 4, 8, 12 | 168 | 1/7 |

EXAMPLE 10

Pharmaceutical Composition: Injectable Solution

| | |
|---|---|
| Compound of the Example | 10 mg |
| Distilled water for injectable preparations | 25 ml |

What is claimed is:

1. A compound selected from those of formula (I):

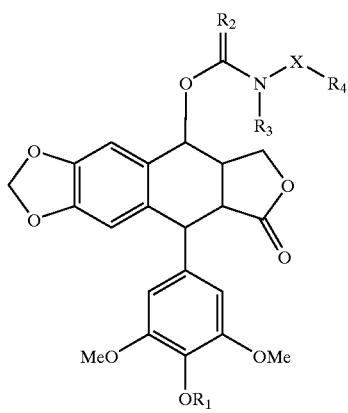

(I)

wherein:

$R_1$ represents hydrogen, linear or branched ($C_1$-$C_6$)alkyl, aryl, aryl-($C_1$-$C_6$)alkyl in which the alkyl moiety may be linear or branched, heteroaryl, heteroaryl-($C_1$-$C_6$) alkyl in which the alkyl moiety may be linear or branched, linear or branched ($C_1$-$C_6$)alkoxycarbonyl, aryloxycarbonyl, aryl-($C_1$-$C_6$)alkoxycarbonyl in which the alkoxy moiety may be linear or branched, heterocycloalkoxycarbonyl, linear or branched ($C_1$-$C_6$) alkylsulfonyl, arylsulfonyl, aryl-($C_1$-$C_6$)alkylsulfonyl in which the alkyl moiety may be linear or branched, or phosphono, $R_2$ represents oxygen or sulphur, $R_3$ represents hydrogen, linear or branched ($C_1$-$C_6$)alkyl, cycloalkyl or aryl-($C_1$-$C_6$)alkyl in which the alkyl moiety may be linear or branched, X represents linear or branched ($C_1$-$C_6$)alkylene, $R_4$ represents:
—amino optionally substituted by one or two identical or different groups selected from linear or branched ($C_1$-$C_6$)alkyl, aryl, or aryl-($C_1$-$C_6$)alkyl in which the alkyl moiety may be linear or branched,
—N($R_3$)—$X_1$—$OR_5$ wherein $R_3$ is as defined hereinbefore, $X_1$ represents a linear or branched ($C_1$-$C_6$)alkylene and $R_5$ represents hydrogen, linear or branched ($C_1$-$C_6$)alkyl, aryl, or aryl-($C_1$-$C_6$)alkyl in which the alkyl moiety may be linear or branched,
—N($R_3$)—$X_1$—$NR_6R_7$ wherein $R_3$ and $X_1$ are as defined hereinbefore and $R_6$ and $R_7$, which may be identical or different, each represents hydrogen, linear or branched ($C_1$-$C_6$)alkyl, aryl, or aryl-($C_1$-$C_6$) alkyl in which the alkyl moiety may be linear or branched, hydroxy, linear or branched ($C_1$-$C_6$)alkoxy, aryloxy, —O—$X_1$—$OR_5$ wherein $R_5$ and $X_1$ are as defined hereinbefore, or —O—$X_1$—$NR_6R_7$ wherein $R_6$, $R_7$ and $X_1$ are as defined hereinbefore, its isomers, and addition salts thereof with a pharmaceutically acceptable acid or base, wherein:

aryl denotes phenyl, biphenyl, naphthyl, dihydronaphthyl, tetrahydronaphthyl, indenyl, indanyl and benzocyclobutyl, each group optionally having one or more identical or different substituents selected from halogen, hydroxy, linear or branched ($C_1$-$C_6$)alkyl, linear or branched ($C_1$-$C_6$)alkoxy, cyano, nitro, amino, linear or branched ($C_1$-$C_6$)alkyl-amino, di-($C_1$-$C_6$) alkylamino in which each alkyl moiety may be linear or branched, carboxy, linear or branched ($C_1$-$C_6$) alkoxycarbonyl, linear or branched ($C_1$-$C_6$) trihaloalkyl, linear or branched ($C_1$-$C_6$) alkylcarbonyloxy, linear or branched ($C_1$-$C_6$) alkylcarbonyl, and aminocarbonyl in which the amino moiety is optionally substituted by one or two identical or different linear or branched ($C_1$-$C_6$)alkyl, heteroaryl denotes an aromatic monocyclic group, aromatic bicyclic group, or bicyclic group in which one of the rings is aromatic and the other ring is partially hydrogenated, each of which groups has from 5 to 12 ring members and contains in the ring system one, two or three hetero atoms selected from oxygen, nitrogen and sulphur, it being possible for the heteroaryl optionally to be substituted by the same substituents such as those decribed in the definition of the aryl group, cycloalkyl denotes a 3 to 10 carbon monocyclic or bicyclic group that is saturated or unsaturated, but not of aromatic character, which group is optionally substituted by one or more identical or different groups selected from halogen, linear or branched ($C_1$-$C_6$) alkyl, linear or branched ($C_1$-$C_6$)trihaloalkyl, hydroxy, amino, linear or branched ($C_1$-$C_6$)alkylamino and di-($C_1$-$C_6$)alkylamino in which each alkyl moiety may be linear or branched, heterocycloalkyl denotes a cycloalkyl group as defined above optionally substituted in the ring system by one or two hetero atoms selected from oxygen, nitrogen and sulphur, the heterocycloalkyl being optionally substituted by one or more substituents such as those described in the definition of the cycloalkyl group, and isomers denotes enantiomers and diastereoisomers.

2. A compound of claim 1, wherein $R_1$ represents hydrogen.

3. A compound of claim 1, wherein $R_2$ represents oxygen.

4. A compound of claim 1, wherein X represents linear ($C_2$-$C_4$)alkylene.

5. A compound of claim 1, wherein $R_3$ represents hydrogen or linear or branched ($C_1$-$C_6$) alkyl.

6. A compound of claim 1, wherein $R_4$ is selected from:
amino substituted by one or two identical or different linear or branched ($C_1$-$C_6$)alkyl groups, —N($R_3$)—$X_1$—$OR_5$ wherein $R_3$ represents hydrogen or linear or branched ($C_1$–$C_6$)alkyl, and —O—$X_1$—$OR_5$.

7. A compound of claim 1, wherein $R_4$ represents —N($R_3$)—$X_1$—$OR_5$, or —O—$X_1$—$OR_5$, wherein $R_3$ represents hydrogen, $X_1$ represents linear ($C_2$–$C_4$)alkylene chain, and $R_5$ represents hydrogen.

8. A compound of claim 1 selected from:

(5S,5aS,8aS,9R)-9-(4-hydroxy-3,5-dimethoxyphenyl)-8-oxo-5,5a,6,8,8a,9-hexahydrofuro[3',4':6,7]naphtho[2,3-d][1,3]dioxol-5-yl 2-(dimethylamino)ethyl(methyl)carbamate, (5S,5aS,8aR,9R)-9-(4-hydroxy-3,5-dimethoxyphenyl)-8-oxo-5,5a,6,8,8a,9-hexahydrofuro[3',4':6,7]naphtho[2,3-d][1,3]dioxol-5-yl 2-(dimethylamino)ethyl(methyl)carbamate, (5S,5aS,8aS,9R)-9-(4-hydroxy-3,5-dimethoxyphenyl)-8-oxo-5,5a,6,8,8a,9-hexahydrofuro[3',4':6,7]naphtho[2,3-d][1,3]dioxol-5-yl 3-(dimethylamino)propylcarbamate, (5S,5aS,8aS,9R)-9-(4-hydroxy-3,5-dimethoxyphenyl)-8-oxo-5,5a,6,8,8a,9-hexahydrofuro[3',4':6,7]naphtho[2,3-d][1,3]dioxol-5-yl 2-(2-hydroxyethoxy)ethylcarbamate, (5S,5aS,8aS,9R)-9-(4-hydroxy-3,5-dimethoxyphenyl)-8-oxo-5,5a,6,8,8a,9-hexa-hydrofuro[3',4':6,7]naphtho[2,3-d][1,3]dioxol-5-yl 2-[(2-hydroxyethyl)amino]ethylcarbamate, and (5S,5aS,8aS,9R)-9-(4-hydroxy-3,5-dimethoxyphenyl)-8-oxo-5,5a,6,8,8a,9-hexahydrofuro[3',4':6,7]naphtho[2,3-d][1,3]dioxol-5-yl 2-(dimethylamino)ethylcarbamate, and its isomers, and addition salts thereof with a pharmaceutically acceptable acid or base.

9. A method for treating a living animal body afflicted with cancer comprising the step of administering to the living animal body an amount of a compound of claim 1 which is effective for alleviation of the cancer.

10. A pharmaceutical composition useful in treating cancer comprising as active principle an effective amount of a compound of claim 1, together with one or more pharmaceutically-acceptable excipients of vehicles.

* * * * *